United States Patent [19]

Johal

[11] 4,334,024

[45] Jun. 8, 1982

[54] PREPARATION AND CRYSTALLIZATION OF FRACTION I PROTEIN FROM PLANT SOURCES

[76] Inventor: Sarjit Johal, 1411 S. 11th St. #2, Lincoln, Nebr. 86502

[21] Appl. No.: 203,779

[22] Filed: Nov. 3, 1980

[51] Int. Cl.$^3$ .............................................. C12N 9/88
[52] U.S. Cl. ..................................... 435/232; 435/816
[58] Field of Search ................................ 435/232, 816

[56] References Cited

U.S. PATENT DOCUMENTS

| | | | |
|---|---|---|---|
| 2,600,903 | 6/1952 | Miller | 426/655 X |
| 3,780,183 | 12/1973 | Edwards et al. | 426/50 |
| 3,823,128 | 7/1974 | Bickoff et al. | 260/112 R |
| 4,268,632 | 5/1981 | Wildman et al. | 435/232 |

OTHER PUBLICATIONS

Paulsen et al., Biochemistry, vol. 5, pp. 2350–2357, Jul. 1966.
Chan et al., Science, vol. 176, pp. 1145–1146, (1972).
Johal et al., Science, vol. 204, pp. 75–77, (Apr. 1979).
Kung et al. in Methods of Enzymology, vol. 69, pp. 326–336, (1980).

*Primary Examiner*—Lionel M. Shapiro

[57] ABSTRACT

A single, simple, uniform protocol for the rapid large scale purification and crystallization of ribulose 1,5-bisphosphate carboxylase (RuBisCO) to a greater than 90% purity from a wide variety of plant species, involving the steps of grinding and homogenizing plant material, such as leaves, with a suitable, acqueous buffer solution. The solution is filtered and the residue discarded. While maintaining temperature and pH control, sufficient quantities of polyethylene glycol (PEG) are added while stirring to bring the final concentration of PEG in the range of 8 to 15 (weight/volume) percent. To enhance crystal formation, magnesium chloride can be added to the solution. The precipitated material is discarded and the pure RuBisCO crystals which separate out of the remaining supernatant are collected, washed, dried and stored.

16 Claims, No Drawings

PREPARATION AND CRYSTALLIZATION OF FRACTION I PROTEIN FROM PLANT SOURCES

BACKGROUND OF THE INVENTION

This invention relates to a method of preparing and crystallizing Fraction I protein directly from unpurified extracts of a variety of plant species.

With the cost and inefficiency involved in the production of animal protein for human consumption and with the steady growth of world population, and increased usage of protein resources, it is becoming more apparent that nonconventional sources must be tapped for the production of high quality proteins that meet industrial needs as well as the nutritional standards and requirements for both human and animal consumption. Within the last thirty or so years, as the need for new sources of high quality protein has become crucial, terrestrial and aquatic plants have been seriously investigated as possible protein sources. Leaves of all plants contain certain soluble proteins that are generally rich in the essential amino acids and thus offer a high potential for the increased production of high quality protein for human and animal dietary needs and at affordable prices.

It is well-known in the art that considerable amounts of protein can be recovered from forage crops without destroying or decreasing their value as fodder or silage, by suitably modifying and improving available processing techniques. Under most current agricultural practices, however, valuable proteins obtainable from plants and forage crops are discarded and thus wasted.

In recent times, however, some techniques have been developed for the production of plant proteins. Such known techniques do not involve separating or identifying the nature, type and quality of the resulting proteins. Thus, such protein-rich products are in a form that is generally not of the highest quality and therefor unsuitable for human consumption. One such simple procedure for the preparation of a protein from the leaves of alfalfa consists of obtaining therefrom a dark green non-protein fraction that may be dried and used as animal fodder, and a white, bland, protein-rich fraction which is insoluble. Due to its insolubility, the protein-rich fraction is particularly unsuitable for human and anminal consumption as a food additive or fortifier.

The most abundant major plant protein is Fraction 1 protein. Its major component has been identified as the enzyme ribulose 1,5-bisphosphate carboxylase (RuBisCO). Fraction 1 protein is widely distributed in nature and constitutes up to 50% of the soluble protein contained in leaves and approximately 20% of the total plant protein. The amino acid composition of Fraction 1 protein is well balanced in terms of the essential and non-essential amino acids, comparing favorably with soybean, casein and animal proteins. The amounts of the essential amino acids in Fraction 1 protein, with the exception of methionine, meet or even exceed standards established for human nutritional requirements. The protein also has potential utility in the medical field.

Before its usefulness and possible incorporation as a food supplement can be laboratory and field tested this major important protein must be isolated and purified in large quantifies. It is essential that the protein be in a relatively pure form. However, current purification techniques are not applicable to large-scale isolation of RuBisCO in a pure form. Most published procedures for purifying Fraction 1 protein and its major component, RuBisCO, generally use small quantities of leaf tissue and require fairly elaborate analytical techniques such as ultracentrifugation and chromatography or sucrose gradient fractionation. While these procedures are useful for obtaining quantites of RuBisCO on a small laboratory scale sufficient for structural and enzymatic studies, they are incapable of purifying large quantities of the enzyme. It is physically impossible to scale-up most of these analytical methods to isolate and purify the enzyme in relatively pure form for its effective utilization in human and animal diets.

RuBisCO has also been crystallized, on the same analytical scale, using pre-purified extracts of seven plant species consisting of spinach, alfalfa, tomato, potato, corn, cotton, and tobacco. Such known methods have not been successful in the preparation of RuBisCO on a large, manufacturing scale nor have they been demonstrated to be effective in purifying the enzyme from unpurified extracts of plant species.

Currently only the RuBisCO from tobacco plants can be crystallized from unpurified extracts. The procedural steps heretofore used in the preparation of the crystalline tobacco enzyme involve the steps of (1) breaking the chloroplasts in the presence of high concentrations of sodium chloride to release the enzyme, (2) heating the resulting solution to precipitate all other undesirable components, (3) removing the excess sodium chloride by gel filtration, and (4) allowing the protein crystals to form.

However, crystallization is a complex phenomena and the molecular forces which cause proteins in general to crystallize are poorly understood. Solubility and viscosity properties of proteins differ from one protein to another and depend on the primary, secondary, tertiary (and where applicable), quarternary structures of the specific proteins. The nature and concentration of electrolytes present in the medium, the pH temperature, and concentration of the protein are crucial factors which influence the crystallization process. The choice of the precipitant employed in initiating nucleation and crystallization of proteins also plays an important role.

The optimum concentrations of these various reactants which are effective for one protein may or may not be effective for other proteins, due to wide variations in their structures. In addition, proteins are very sensitive to heat and chemicals which can cause their denaturation. Each protein, or even the same protein derived from different species, may vary in their primary, secondary, and tertiary structures and generally must be studied separately and independently to determine their structural and chemcial properties.

Existing procedures for the crystallization of tobacco RuBisCO, while a significant improvement over other earlier techniques, suffers many of the aforementioned drawbacks and is of limited utility. For instance the process can only be used successfully with tobacco leaves that are no more than 3-4 months old, such leaves being unavailable under current agricultural practices. All other sources of RuBisCO have proven unsatisfactory to crystallization by this procedure.

The need for gel filtration and the inherent limitations in using this step severely limit the total quantity of material processed. Furthermore the tobacco RuBisCO crystals obtained in this manner are not stable to lyophilization, which produces a powder that is insoluble, precluding its use in many formulations and as a food additive. Since the crystals have not been found to be capable of being freeze-dried, the nutritional value of the crystals may be diminished because 70% of the volume is aqueous. Storage and transfer may also become a problem.

Thus, there is a continual need for a method of preparation and crystallization of Fraction 1 protein and RuBisCO in sufficiently large quantities to enable its utilization as a major protein source for animal and human consumption.

DESCRIPTION OF THE PRIOR ART

U.S. Pat. No. 2,600,903 issued Mar. 26, 1948 to Miller disclosed a method for extracting alfalfa juice of high nutritional quality from freshly harvested alfalfa, involving adjusting the raw juice to an alkaline pH, concentrating and recovering the juice after separating the precipitated solids.

U.S. Pat. No. 3,780,183 issued Dec. 18, 1973, to Edwards teaches a method of preparing aqueous, alkaline solutions of alfalfa and clover, by subjection the solution to digestion with pancreatin or a similar proteolytic enzyme and separating the soluble and insoluble portions, both of which have been found to have nutritional value.

U.S. Pat. No. 3,823,128 issued July 9, 1974 to Bickoff et al., discloses a method for the fractionation of alfalfa and other leafy green crops, for the isolation and purification of a protein fraction free from chlorophyll and other pigments, cellulose fibers and other components unsuitable for human consumption.

Paulsen and Lane, Biochemistry, 5,2350 (1966) present a protocol for purifying spinach-bisphosphate-carboxylase in quantities sufficient for enzymatic studies.

Chan et al., [P. H. Chan, K. Sakano, S. Singh and S. G. Wildman], Science, 176, 1145 (1972) describe a method for crystallization of tobacco-bisphosphate-carboxylase using a low salt dialysis technique and partially purified enzyme as starting material.

Johal and Borque, Science, 204, 75 (1979), reported crystallization of spinach Fraction 1 protein on an analytical and preparative scale using prepurified enzyme and an equilibrium vapor diffusion technique with polyethylene glycol as a precipitant.

Kung et al., [S. D. Kung, R. Chollet and T-V. Marsho, methods of Enzymology, vol-69, 326 (1980)] described a simplified method for the crystallization and assay of Tobacco Ribulose-bisphosphate carboxylase-oxygenase.

SUMMARY OF THE INVENTION

The subject invention provides a single, simple, uniform protocol for the rapid large scale purification and crystallization of ribulose 1,5-bisphosphate carboxylase (RuBisCO) to a greater than 90% purity from a wide variety of plant species.

According to the subject method, a sample of plant material, preferably leaves, is ground and homogenized with a suitable, aqueous buffer solution, the solution filtered and the residue discarded. The solution is preferably maintained at a temperature in the range of about 4° C. to 25° C. and at a pH between 7.5 and 8.5. Sufficient quantities of polyethylene glycol (PEG) preferably in the 6000 molecular weight range, are added, while stirring, to bring the final concentration of PEG in the range of 8 to 15 (weight/volume) percent, preferably in the 11-14 percent range. To enhance crystal formation, 0.01 to 0.04 M magnesium chloride can be added to the solution. The precipitated material is discarded and the supernatant is stored at about 4° C. for about 2 to 8 hours. The pure RuBisCO crystals which separate out are collected, washed, dried and stored.

The subject method is a major improvement over prior art methods and offers the advantage of being a simple protocol which eliminates sophisticated technology and laborious, time consuming steps. It is suitable for the preparation of better than >90% pure RuBisCO crystals on a large scale and from a wide variety of plant species.

DESCRIPTION OF THE PREFERRED EMBODIMENTS

In the preferred embodiment, the subject method involves bringing the crude leaf extracts of any of several plant species separately or combined, after initially clarifying them by filtration and low speed centrifugation, into contact with a predetermined final concentration of polyethylene glycol, preferably in a two stage process. By allowing the extracts to stand for about 6-8 hours at a temperature of about 4° C., crystals of RuBisCO separate out to be collected. After being washed several times, the crystals can then be used directly, stored at about 4° C. or lyophilized and stored as a powder for future use.

According to the subject method, a sample of plant material, preferably leaves, is homogenized in a suitable aqueous buffer solution, preferably Tris HCl or phosphate or borate in the concentration range of 0.05 to 0.2 M, preferably 0.1 M, and at a pH in the range of 7.5 to 8.5, preferably 7.8 to 8.25, more preferably about 8.2. The homogenate is filtered and the residue is discarded. The filtrate is maintained at a cool temperature, preferably between 2° C. to 7° C., more preferably about 4° C. Sufficient quantities of polyethylene glycol (PEG) in the molecular range of about 5000 to 7000, preferably 6000, are added to the filtrate to bring the range of the final concentration of PEG to between 5 and 15 (weight/volume) percent, preferably in the 8-15 (weight/volume) percent range and more preferably 11-14 (weight/volume) percent, still more preferably in the 12-13 (weight/volume) percent rance. Addition of magnesium chloride in the concentration range of 0.01 to 0.04 M, preferably 0.02 to 0.03 M, following the addition of PEG enhances crystal formation and yield.

The precipitated material is discarded and the supernatant is stored at a temperature of about 4° C. for about 2-10 hours, preferably about 6 to 8 hours. Pure RuBisCO crystals which separate out are collected, washed and stored or lyophilized and stored.

The crystal preparation so obtained are homogeneous and have a carboxylase activity comparable to crystalline preparations made by other, more elaborate techniques. This technique has been successful in the preparation of RuBisCO from ryegrass, alfalfa, spinach, oats, peas, tomato, potato, *Moricandia arvensis* and tobacco and is applicable to other plant species as well. In addition, the leaves of several plant species can be combined and crystalline RuBisCO obtained by use of the subject matter.

Several factors have been found to affect crystallization of the protein. Crystal yields were considerably enhanced when the pH was maintained at or near 8.2, although a pH range of from about 7.5 to 8.5 was quite satisfactory. The optimum concentration range for the precipitant was between 5 and 15 (weight/volume) percent, more generally 8-15 (weight/volume) percent, preferably 11-14 percent, more preferably 12-13

(weight/volume) percent. Polyethylene glycol (PEG) and ammonium sulfate have both been found to be effective precipitants, depending upon the species under study. Of the various PEG's tested, namely, PEG 600, 1000, 2000, 4000 and 6000, PEG 6000 was the most effective precipitant. The temperature range found to be most conducive to crystallization was from about 2° C. to about 7° C., preferably around 4° C.

Most conventional buffers are suitable but Tris-HCl, phosphate or borate buffers were preferred. Addition of magnesium chloride in the concentration range of 0.01 to 0.04 M, preferably 0.02 to 0.03 M immediately following the addition of PEG was found to enhance crystallization.

Addition of PEG may be accomplished in two stages but a two stage addition is not a critical factor in the crystallization process. However, the two stage addition reduces centrifugation time and the "g" values employed. The initial addition also effectively precipitates, membranes or organelles which may interefere with crystal yields. The final concentration of PEG is critical for the effective crystallization of RuBisCO. In particular, final PEG concentration less than 5 percent has been found to decrease crystal yields. The physical state of the plant or condition or the leaves and the origin of species, do not affect crystallization by the subject method.

The following examples are included to demonstrate the effectiveness of the method and are not to be construed so as to limit in any manner the nature or scope of the method or the appended claims.

EXPERIMENTAL

General Protocol

Experiment 1

100 gms of fresh leaves are homogenized in a cold Waring blendor at about 4° C. with 300 mls of 0.1 M Tris-HCl buffer containing small amounts of (e.g., 0.2 M) sodium chloride and sodium thio-sulfate, for about 1 or 2 minutes. The resulting slurry is squeezed through three or four layers of cheesecloth. Sufficient amounts of Polyethylene glycol (PEG) 6000 and magnesium chloride ($MgCl_2$) are then added to the green filtrate while stirring slowly at or near room temperature to bring the solution to 10 (weight/volume) percent PEG and 0.03 M $MgCl_2$.

The green suspension is centrifuged at about 4° C. and 12,000 g for about 10 minutes. The precipitates formed are discarded. Further amounts of PEG 6000 are added to the supernatant while stirring slowly to bring the final concentration of PEG 6000 to 12–13 (weight/volume) percent. The resulting solution is stored at about 4° C. Crystals of RuBisCO, which separate out, are collected, washed and ready for use of storage of lyophilized and stored as a powder. The mother liquor or supernatant is still rich in other proteins, nucleic acids and sugars and may be lyophilized or heat dried and used for feed.

The procedure as sent for the above, is schematically represented below:

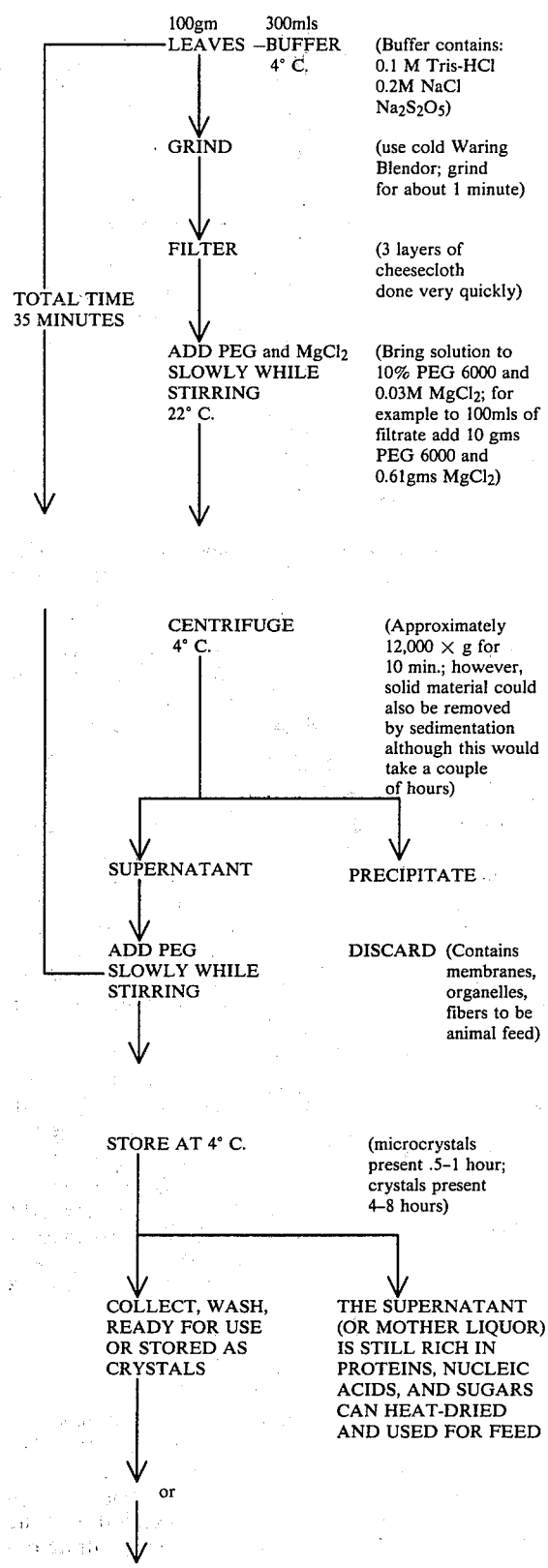

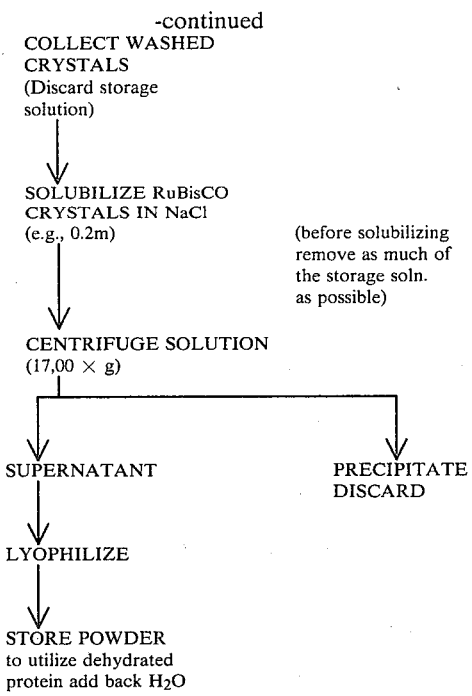

Some specific data, i.e., the time required to sufficiently grind leaf tissue, the volume of the filtrate, the volume of the supernatant recovered after centrifugation, and the quantity of crystals recovered will vary somewhat from species to species. However, certain other parameters such as the buffer, the quantities of polyethylene glycol 6000 and $MgCl_2$, the crystallization time are relatively constant and not species dependent.

The resulting crystals have been found to be pure ribulose 1,5-bisphosphate carboxylase/oxygenase, as determined by isoelectric focusing, polyacrylamide gel electrophoresis, and SDS-polyacrylamide gel electrophoresis. Carboxylase activity assays indicate that the crystalline enzyme is active and not denatured or modified during the purification/crystallization process. Examination of the supernatant (i.e., mother liquor after ribulose 1,5-bisphosphate carboxylase/oxygenase crystallization) reveals that essentially all (>90%) of the enzyme has been removed from solution while all other proteins appear intact.

Thus, ribulose 1,5-bisphosphate carboxylase/oxygenase which comprises 40–55% of the total soluble leaf protein and approximately 20% of the total leaf protein can be easily purified and crystallized by this procedure. The process can be scaled-up, although experiments to date have had a maximum of 300 gms of leaves, or scaled-down, a minimum of 7 gms, with no apparent limiting factors. In addition, the other leaf components can also be retained for other uses such as forage and extraction of leaf proteins by conventional techniques such as heat or acid precipitation.

Experiment 2

RuBisCO from Ryegrass (*Lolium gremie* L.)

9 gms of Ryegrass leaves are homogenized in a cold Waring blendor at about 4° C., with 65 ml of 0.1 M of Tris-HCl buffer containing 0.2 M NaCl and small amounts of sodium meta-bisulfate. The resulting slurry is filtered through three layers of cheesecloth and the residue is discarded. To 58 ml of the green filtrate obtained are added, while slowly stirring on ice, 27 ml of a 20 (weight/volume) percent PEG solution and 1.8 ml of a 2 M $MgCl_2$ solution. The resulting slurry is centrifuged for about 5 min. at 14,000 g. To the supernatant, an additional 1.74 gms of solid PEG 6000 are added, while slowly stirring on ice. 0.22 gm incremented additions of solid PEG 6000 are continued until microcrystalline material is observed in the solution. The solution is left overnight in the cold room or refrigerator. The RuBisCO crystals formed are collected, washed and stored.

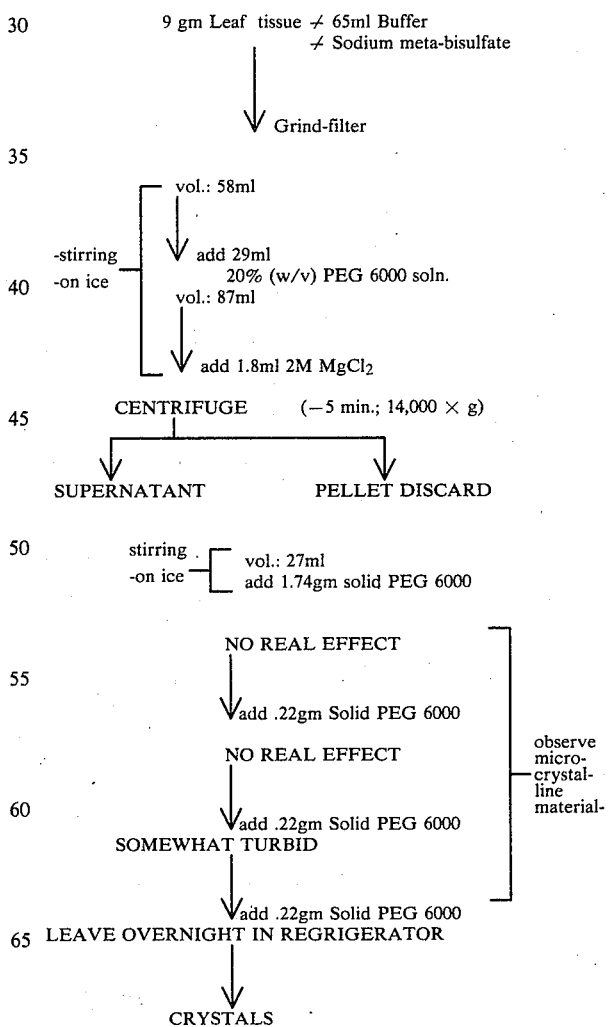

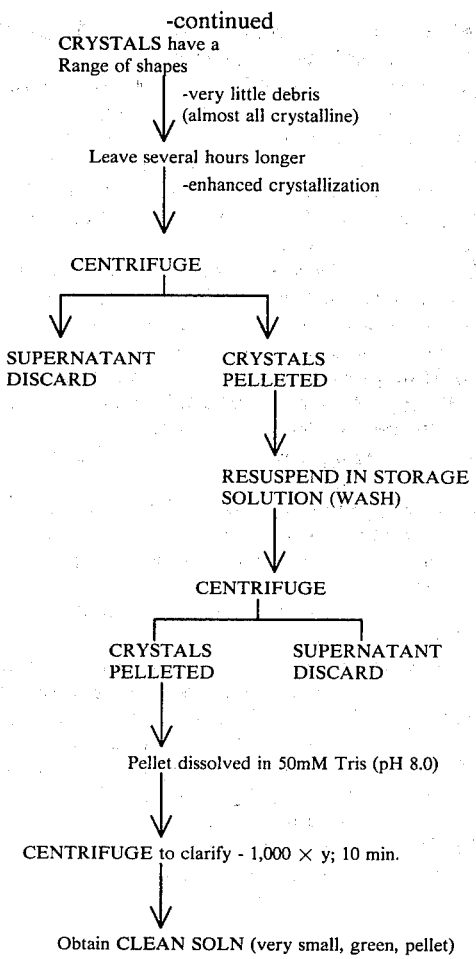

Experiment 3

RuBisCO Crystals From A Crucifer, *Moricandia Arvensis*

40 gm *Moricandia arvensis* leaves are ground in a cold Waring blendor at 4° C., with 150 ml of buffer containing 0.2 M NaCl and 0.51 gm sodium metabisulfate. The resulting slurry is filtered through three layers of cheesecloth and the residue discarded. To 160 ml of the crude homogenate are added 80 ml of a 20% (weight/volume) PEG 6000 solution and 3.7 ml of a 2 M solution of $MgCl_2$. The solution is allowed to stand for about 1 or 2 minutes and centrifuged for about 15 min. at 9,000 RPM. To the Supernatant, 3.54 gm of solid PEG 6000 are added while stirring until completely solubilized. Further amounts of 1.18 gm and 1.1 gm PEG 6000 are added while stirring. The solution slowly turns cloudy and crystals of RuBisCO are observed within 2 hours.

The procedure is shown schematically as follows:

```
                (Blender - Buffer - cold)
                40gm leaves + 150ml buffer
                (.51gm Na metabusulfate)
                (Na2S2O5)
                Grind - Filter
    RT
                vol.: (60ml (crude homogenate)
                add 80ml of 20% (w/v) PEG 6000 soln + 3.7ml
                MgCl2 soln.
                (allowed to stand at room temperature for approximately 1.0 minute)
                CENTRIFUGE: 15 min. - 9,000RPM (GSA)
                vol.: 236ml At Room Temperature
                    Add 3.54gm PEG     solubilize completely
                    Add 1.18gm PEG     solubilize completely
                    Add 1.1gm PEG      solubilize completely
                Solution appears clean - then slowly turns cloudy;
                Crystals observed within 2 hours
```

Experiment 4

RuBisCO from tobacco (*Nicotina tabacum*) and ryegrass (*Lilium gremie* L.) combined.

18 gm of tobacco leaves are combined with 45 gms of ryegrass leaves and are homogenized in a cold Waring blendor at about 4° C., with 250 ml of 0.1 M Tris-HCl buffer containing 0.2 M NaCl and small amounts of sodium meta-bisulfate. The resulting slurry is filtered through three layers of cheesecloth and the residue is discarded. To 265 ml of the green filtrate obtained are added 130 ml of 20 (weight/volume) percent PEG solution and 5.8 ml of 2 M $MgCl_2$ solution while slowly stirring on ice. An additional 3.9 gm of solid PEG 6000 is added while stirring. The solution turns slightly turbid and is refrigerated. The RuBisCO crystals of tobacco and ryegrass formed are collected, washed and stored.

Analytical techniques, e.g., SDS gel electrophoresis and isoelectric focusing, reveal that both tobacco and ryegrass crystals formed.

The subject method thus provides decided advantages over prior art methods. It eliminates several laborious, time consuming steps and simplifies the crystallization process considerably. The method is also adoptable for any convenient sample size.

While the above description provides a full and complete disclosure of the preferred embodiments of the subject invention, various modifications, alternative constructions, equivalents and improvements may be practised without departing from the spirit and scope of the appended claims.

What is claimed:

1. A method for preparing crystalline ribulose 1,5-bisphosphate carboxylase from plant material comprising the steps of:
   (a) grinding a sample of said plant material with a suitable buffer solution;
   (b) filtering said solution;
   (c) adding to said solution, while stirring, sufficient quantities of polyethylene glycol (PEG) having a molecular weight in the range from 5000 to 7000 to bring said polyethylene glycol to a final concentration in the range from 5 to 15 (weight/volume) percent;
   (d) discarding the precipitates formed;
   (e) storing said solution for about 1 to 8 hours;
   (f) collecting and washing the crystals resulting from said storage; and
   (g) lyophilizing said crystals.

2. A method according to claim 1, wherein magnesium chloride in the concentration range of about 0.01 to 0.04 is added to said solution immediately following the addition of said PEG.

3. A method according to claim 1, wherein the storage temperature of said solution is about 4° C. and the pH is about 7.5 to 8.5.

4. A method for the preparation and crystallization of RuBisCo from extracts of plant material comprising:
 (a) grinding a sample of said plant material with an aqueous buffer solution;
 (b) filtering said solution;
 (c) adding to said solution polyethylene glycol slowly having a molecular weight in the range from 5000 to 7000, while stirring, to a final concentration in the range from 5 to 18 (weight/volume) percent;
 (d) centrifuging said solution;
 (e) discarding the precipitates formed;
 (f) adding to the filtrate, further amounts of polyethylene glycol while stirring;
 (g) maintaining said filtrate at a cool temperature;
 (h) collecting and washing the crystals formed; and
 (i) lyophilizing crystals and storing as a powder.

5. A method according to claim 4, wherein magnesium chloride was included subsequent to the addition of said polyethylene glycol.

6. A method according to claim 5, wherein said magnesium chloride is in the concentration range of about 0.01 to about 0.04 M.

7. A method according to claim 4, wherein said buffer is selected from a group consisting of Tris-HCl, phosphate, carbonate and borate.

8. A method according to claim 7, wherein said buffer concentration range of about 0.01 M to 0.2 M and the pH of said buffer is in the range of 7.5 to 8.5.

9. A method according to claim 4, wherein said plant material is in the form of leaves.

10. A method according to claim 4, wherein the pH of said solution is in the range of 7.8 to 8.2.

11. A method according to claim 4, wherein said filtrate in Step (g) is maintained at a temperature of from about 2° C. to about 8° C. for about 1 to about 8 hours.

12. A method according to claim 4, wherein said plant material is selected from a group consisting of tobacco, spinach, alfalfa, oats, *Moricandia arvensis*, peas, tomato, potato and ryegrass.

13. In the method of preparing ribulose 1,5-bisphosphate carboxylase from alkaline homogenates of alfalfa, spinach, tobacco, tomato, ryegrass and corn, the improvement comprising the steps of:
 (a) treating said alkaline homogenate with polyethylene glycol having a molecular weight in the range from 5000 to 7000, while stirring;
 (b) centrifuging said homogenate and discarding the precipitates;
 (c) adding to the supernatant further amounts of said polyethylene glycol to a final concentration in the range from 5 to 18 (weight/volume) percent while stirring;
 (d) maintaining said solution at about 4° C. for about 2-8 hours; and
 (e) separating and washing the crystals formed.

14. The improvement according to claim 13, wherein magnesium chloride is added to said solution subsequent to the addition of said polyethylene glycol in step (a).

15. The improvement according to claim 14, wherein the concentration of said magnesium chloride is in the range of about 0.01 to 0.04 M.

16. The improvement according to claim 13, wherein the pH of said homogenate is about 8.2.

* * * * *